United States Patent [19]
Goetz et al.

[11] 3,965,193
[45] June 22, 1976

[54] PRODUCTION OF HIGH MOLECULAR WEIGHT α,β-UNSATURATED ALDEHYDES

[75] Inventors: Norbert Goetz, Bobenheim-Roxheim; Roman Fischer, Ludwigshafen, both of Germany

[73] Assignee: Badische Anilin- & Soda-Fabrik Aktiengesellschaft, Ludwigshafen (Rhine), Germany

[22] Filed: Nov. 1, 1972

[21] Appl. No.: 302,650

[30] Foreign Application Priority Data
Nov. 17, 1971  Germany............................. 2157035
Oct. 9, 1972   Germany............................. 2249372
Oct. 9, 1972   Germany............................. 2249398

[52] U.S. Cl............................. 260/598; 260/483; 260/599; 260/601 R; 260/614 R
[51] Int. Cl.$^2$.................. C07C 47/38; C07C 47/20; C07C 47/52
[58] Field of Search................. 260/601 R, 598, 599

[56] References Cited
FOREIGN PATENTS OR APPLICATIONS
1,020,728    2/1966   United Kingdom

OTHER PUBLICATIONS

Fuson, "Advanced Organic Chemistry", pp. 499 & 500, Wiley, N.Y., N.Y. (1950).

Fuson, "Chemical Reviews", vol. 16, pp. 1–26, (1947).

*Primary Examiner*—Raymond V. Rush
*Assistant Examiner*—D. B. Springer
*Attorney, Agent, or Firm*—Johnston, Keil, Thompson & Shurtleff

[57] ABSTRACT

A process for the production of high molecular weight α, β-unsaturated aldehydes by alkylation of the γ-carbon atom of a lower molecular weight α, β-unsaturated aldehyde with a substituted allyl alcohol which has a chain branching in the 3-position carbon atom or a phenyl radical in the 3-position or of a corresponding allyl alcohol carboxylic ester at elevated temperature in the liquid phase.

The products are valuable intermediates for the production of natural substances and odorants.

12 Claims, No Drawings

PRODUCTION OF HIGH MOLECULAR WEIGHT α, β-UNSATURATED ALDEHYDES

The invention relates to a process for the production of high molecular weight α,β-unsaturated aldehydes by alkylation of α,β-unsaturated aldehydes with a substituted allyl alcohol which has a branch in the chain on the carbon atom in the 3-position or a phenyl radial in the 3-position, or a corresponding allyl alcohol carboxylic ester at elevated temperature.

The reaction of isobutyraldehyde with allyl alcohol in the presence of activated carbon or silica gel in the gas phase is disclosed in U.S. Pat. No. 2,957,028.

Furthermore U.S. Pat. No. 3,335,187 discloses the vapor phase reaction of saturated aliphatic aldehydes with allyl alcohol in the presence of an activated carbon or silica gel catalyst which has been impregnated with special acid inorganic compounds. In both patents a reaction of saturated aldehydes with allyl alcohol is described in which the aldehyde is alkylated by the alcohol in the α-position to the carbonyl group.

Moreover U.S. Pat. Nos. 2,560,777, 2,710,873 and 2,720,530 disclose the addition of aldehydes to unsaturated compounds in the presence of dibenzoyl peroxide with the formation of the corresponding ketones. For example the acetic ester of 2-methylheptan-6-on-3-ol can be prepared from the acetic ester of 2-methyl-4-penten-3-ol and acetaldehyde by this method.

We have now found that high molecular weight α,β-unsaturated aldehydes of the general formula (I):

$$R^9-C=C-C-C-C=C-C-H \quad \text{(with } R^8, R^7, R^6, R^4, R^2, R^1 \text{ and } R^5, R^3 \text{ substituents and =O)}$$

(I)

in which
$R^1$ is hydrogen, alkyl of one to four carbon atoms, phenyl, or phenyl bearing alkyl as substituent;
$R^2$ is hydrogen, alkyl of one to four carbon atoms, phenyl, or phenyl bearing alkyl as substituent;
$R^3$ is hydrogen or alkyl of one to four carbon atoms;
$R^4$ is hydrogen or a saturated or unsaturated, branched or linear aliphatic or cycloaliphatic hydrocarbon radical of one to twelve carbon atoms;
$R^5$ is hydrogen or alkyl of one to four carbon atoms;
$R^6$ is hydrogen or alkyl of one to four carbon atoms;
$R^7$ is hydrogen or alkyl of one to four carbon atoms;
$R^8$ is alkyl of one to four carbon atoms or (when $R^9$ is phenyl) hydrogen; and
$R^9$ is a saturated or unsaturated, branched or linear aliphatic or cycloaliphatic hydrogen radical of one to twelve carbon atoms in which carbon-carbon bonds may be interrupted by oxygen or the group —O—CO, or phenyl or phenyl bearing alkyl as substituent can be prepared in a simple way by reacting an allyl compound of the general formula (II):

$$R^9-C=C-C-O-R^{10} \quad \text{(with } R^8, R^7, R^6 \text{ and } R^5 \text{ substituents)}$$

(II)

in which $R^5$ to $R^9$ have the meanings given above and $R^{10}$ is hydrogen or acyl of a carboxylic acid of one to five carbon atoms with an α,β-unsaturated aldehyde of the formula (III):

$$H-C-C=C-C-H \quad \text{(with } R^3, R^2, R^1, R^4 \text{ substituents and =O)}$$

(III)

in which $R^1$ to $R^4$ have the meanings given above, at elevated temperature and atmospheric pressure or a superatmospheric pressure of up to 250 atmospheres gauge in the liquid phase.

It is surprising that in the reaction of an α,β-unsaturated aldehyde with an allyl compound of formula (II) it is not alkylation of the α-carbon atom which takes place but consistently alkylation of the γ-carbon atom of the aldehyde, even when the carbon atom in the α-position to the formyl group bears a hydrogen atom.

Suitable starting materials for the process of the invention are allyl compounds of the formula (II):

in which each of $R^5$, $R^6$ and $R^7$ is hydrogen or alkyl of one to four carbon atoms, preferably hydrogen or methyl, $R^8$ is alkyl of one to four carbon atoms, preferably methyl, or (when $R^9$ is phenyl) hydrogen, $R^9$ is a saturated or unsaturated, branched or linear aliphatic or cycloaliphatic radical of one to twelve carbon atoms in which the carbon-carbon bonds may be interrupted by oxygen or the group —O—CO—, phenyl, phenyl bearing alkyl as substituent, or preferably an aliphatic hydrocarbon radical of one to six carbon atoms and $R^{10}$ is hydrogen or acyl of a carboxylic acid of one to five carbon atoms. Allyl alcohols of a total of five to twenty, particularly from five to fifteen, carbon atoms are preferred.

The following are examples: 3-methyl-2-buten-1-ol, 3-methyl-2-penten-1-ol, 3-methyl-2-hexen-1-ol, 4-methyl-3-penten-2-ol, 4-methyl-3-hexen-2-ol, 2,5-dimethyl-4-hexen-3-ol, 2,3-dimethyl-2-buten-1-ol, 3,4-dimethyl-2-penten-1-ol, 4,5-dimethyl-3-hexen-2-ol, 3,4,4-trimethyl-2-penten-1-ol, nerol, 1,1,3-trimethyl-3-cyclohexen-5-ol, geraniol, farnesol, ionylidene-ethanol, 3-methylcinnamic alcohol, cinnamic alcohol, 2-methyl-4-hydroxy-2-buten-1-al-(2′,2′-dimethylpropylene)-acetal, 2,6-dimethyl-8-hydroxy-2,6-octadien-1-al-(2′,2′-dimethylpropylene)-acetal, 3-methyl-1-acetoxy-2-butene, 3-methyl-1-propionyloxy-2-butene, 3-methyl-1-butyryloxy-2-pentene, 4-methyl-2-formyloxy-3-pentene, 3-methyl-5-hydroxy-3-penten-1-al diethylacetal, 4-methyl-2-acryloxy-3-hexene, 2,5-dimethyl-3-dimethylacryloxy 4-hexene, 2,3-dimethyl-1-acetoxy-2-butene, 3,7-dimethyl-1-acetoxy-2,6-octadiene, cinnamic alcohol acetate, 2-methyl-4-acetoxy-2-buten-1-al-(2′,2′-dimethylpropylene)-acetal, 2-methyl-4-methoxy-2-buten-1-ol, 2-methyl-4-acetoxy-2-buten-1-ol and 2-methyl-4-hydroxy-2-buten-1-al-ethyleneacetal.

The reaction with alcohols of formula (IIa):

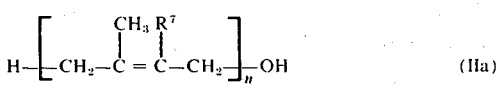

(IIa)

in which n is 1, 2 or 3 and R⁷ is hydrogen or methyl, i.e. the reaction with terpene alcohols such as 3-methyl-2-butene-1-ol, geraniol, farnesol or 2,3-dimethyl-2-buten-1-ol is of particular industrial importance.

The $\alpha,\beta$-unsaturated aldehydes which in accordance with the invention can be reacted with an allyl compound of formula (II) include aldehydes of formula (III):

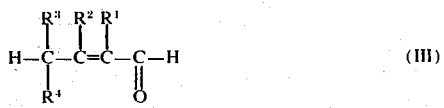

(III)

in which $R^1$ and $R^2$ are hydrogen, alkyl of one to four carbon atoms, phenyl or phenyl bearing alkyl as substituent, preferably hydrogen or methyl, $R^3$ is hydrogen or alkyl of one to four carbon atoms, preferably hydrogen or methyl, and $R^4$ is hydrogen or a saturated or unsaturated, branched or linear aliphatic or cycloaliphatic hydrocarbon radical of one to twelve carbon atoms, preferably hydrogen or an aliphatic hydrocarbon radical of one to five carbon atoms.

Those aldehydes are preferred which in all contain only about four to fifteen, particularly from four to ten, carbon atoms.

Specific examples are: crotonaldehyde, tiglaldehyde, 2-methyl-2-penten-1-al, 2-ethyl-2-hexen-1-al, 3-methyl-3-ethylacrolein, 3,3-diethylacrolein, 3,4-dimethyl-2-penten-1-al, 3,4,4-trimethyl-2-penten-1-al, 2,3-dimethyl-2-buten-1-al, 3-methyl-2-penten-1-al and farnesal, particularly 3,3 dimethylacrolein (3-methyl-2-buten-1-al) and citral.

The process of the invention proceeds particularly advantageously when starting from an $\alpha,\beta$-unsaturated aldehyde which has a chain branching on the carbon atom in the $\beta$-position to the formyl group, i.e. aldehydes of formula (III) in which $R^2$ is not hydrogen but is a hydrocarbon radical of one to eleven carbon atoms, preferably methyl.

The process is carried out by heating the starting compounds for the duration of the reaction at the reaction temperature, if necessary at superatmospheric pressure.

The starting compounds are used with advantage in approximately stoichiometric amounts. The cheaper component may however be used in a one to three molar excess.

The reaction of an allyl compound of formula (II) with an $\alpha,\beta$-unsaturated aldehyde of formula (III) is carried out in the absence of catalysts generally at a temperature of from about 150° to 350°C, preferably from 180° to 300°C, in the liquid phase. It has been found that surprisingly the reaction according to the invention proceeds with better yields and substantially better conversions of the starting products when the reaction is carried out in the presence of an acidic or peroxidic catalyst. When the reaction is carried out in the presence of an acidic or peroxidic catalyst, then somewhat lower temperatures are generally necessary for the reaction. Temperatures of from about 60° to 300°C, preferably from 100° to 250°C, are then used.

Practically all compounds which can split off protons and which upon being dissolved in water can cause by hydrolysis an acid reaction, i.e. a pH from 0 to 6.9 and which do not otherwise attack the reactants when used in the amounts necessary for catalysis are suitable as acid catalysts. Naturally a skilled worker will avoid the use of acids which may decompose under the reaction conditions. Mineral acids and acid salts, heterogeneous acid catalysts and organic acids are all suitable.

Examples of mineral acids are: sulfuric acid, phosphoric acid, hydrogen halides, nitric acid, sulfurous acid, phosphorous acid, perchloric acid, boric acid and silicic acid.

Examples of suitable acid salts are the salts of polybasic acids in which dissociatable hydrogen is only partly replaced by metal such as sodium bisulfate, potassium bisulfate, primary sodium phosphate and sodium bisulfite.

Salts of strong acids with weak bases such as zinc chloride, aluminium chloride and boron trifluoride are also suitable acid salts.

Catalysts such as silica gel, ammonium chloride on activated carbon, sodium bisulfate on activated carbon and acid aluminum oxide are examples of heterogeneous acid catalysts.

The following are examples of groups of organic acids:

Aliphatic monocarboxylic acids such as formic acid, acetic acid, propionic acid, butyric acid, acrylic acid, methacrylic acid, dimethylacrylic acid, chlorinated acetic acids and lactic acid.

Cycloaliphatic monocarboxylic acids such as cyclohexanoic acid.

Araliphatic carboxylic acids such as cinnamic acid and phenylacetic acid.

Aromatic monocarboxylic acids such as benzoic acid, naphthoic acid, salicyclic acid, p-anisic acid and nicotinic acid.

Aliphatic dicarboxylic or tricarboxylic acids such as oxalic acid, malonic acid, succinic acid, adipic acid, citric acid, malic acid and maleic acid.

Aromatic dicarboxylic and tricarboxylic acids such as phthalic acid and terephthalic acid.

Aromatic sulfonic acids such as benzenesulfonic acid and p-toluenesulfonic acid.

Phenols such as phenol, cresols, hydroquinone, chlorophenols, trichlorophenols, nitrophenols and 2,4-dinitrophenol.

Provided the acid does not otherwise attack the reactants under the reaction conditions, the nature of the acid used as catalyst is not critical. The only essential is that a certain concentration, not too high, of hydrogen ions should be present in the reaction mixture. It is best to use a reaction mixture to which such an amount of an acid has been added that a pH of from 1 to 7, preferably from 2 to 5, is present in the reaction mixture. The amount of acid to be used as catalyst depends therefore on the strength of the acid, i.e. on the degree of dissociation of the acid. The reaction according to the invention proceeds particularly advantageously when it is carried out in the presence of from 0.01 to 10%, preferably from 0.1 to 3%, by weight based on the sum of the reactants, of an acid having a pK of from about 3 to 6.

The following are examples of these preferred acids having a pK of from about 3 to 6:
formic acid, propionic acid, butyric acid, benzoic acid, dimethylacrylic acid, succinic acid, adipic acid and acrylic acid.

When using acids of a pK of from about 3 to about 6 which are liquid and which boil at below 200°C such as acetic acid, propionic acid, acrylic acid, dimethylacrylic acid, butyric acid or valeric acid, the reaction may also be carried out by using these acids as solvents at the same time, the allyl acylates being formed intermediately from the allyl alcohols of formula (II) used. The conversions and yields achieved in this variant of the process are however not as good as when using only catalytic amounts of these acids.

When stronger acids are used, i.e acids of a pK of from −9 to about 3, smaller amounts of acid are used because the aldehydes formed are sensitive to these acids.

An advantageous course of the reaction is achieved by carrying out the reaction in the presence of from 0.01 to 1, preferably 0.01 to 0.5% by weight, based on the sum of the reactants, of an acid having a pK of from −9 to about 3.

Examples of these acids of a pK of from −9 to about 3 are: sulfuric acid, phosphoric acid, hydrogen halides, nitric acid, perchloric acid, and oxalic acid.

The use of more weakly acid compounds, i.e. acids of a pK of more than 7 such as phenols is less favorable.

We have also found that the reaction according to the invention also proceeds very advantageously when it is carried out in the presence of hydrogen peroxide in the form of a concentrated aqueous solution or in the presence of an organic peroxy compound.

This fact is particularly surprising because it has to be assumed from the cited literature that in the presence of organic peroxides an addition of the aldehydes to the carbon-carbon double bond of the allyl alcohol would take place with the formation of ketones.

Hydrogen peroxide solutions and organic peroxy compounds are advantageously used in an amount of from 0.1 to 5% and preferably from 0.5 to 3% by weight based on the total of the reactants.

Examples of organic peroxy compounds are di-t-butyl peroxide, t-butyl hydroperoxide, t-butyl peracetate, t-butyl perbenzoate, dibenzoyl peroxide, mono-t-butyl permaleate, dicumyl peroxide, isopropyl percarbonate and cyclohexyl percarbonate.

The organic peroxy compounds do not have to be added as such to the reaction mixture. Another variant of the process, which is also very advantageous, consists in preparing an organic peroxy compound, particularly an aldoperoxide, in the reaction mixture prior to the commencement of the reaction by treatment of the starting materials with oxygen or gas containing oxygen, particularly air. The duration of the treatment is usually from two to thirty minutes, preferably from five to twenty minutes, depending on the strength of the current of gas.

The reaction according to the invention may also be affected favorably either by withdrawing from the reaction equilibrium the water formed in the reaction by adding agents which bind water such as ortho esters, or by removing the water from the reaction mixture by injecting as entrainer a low boiling point hydrocarbon such as pentane, hexane or cyclohexane, continuously as an azeotropic mixture.

The reactants themselves may also be used as an entrainer for water.

It is essential to remove continuously the water formed in the reaction when an allyl compound of the formula (II) in which $R^9$ is a hydrocarbon radical in which carbon-carbon bonds are interrupted by oxgen or the group —O—CO— is reacted in the presence of an acidic or peroxidic catalyst because otherwise most of the ether, acetal and ester groupings are hydrolyzed under the reaction conditions. Cyclic acetal groupings, i.e. acetals of carbonyl compounds with dihydric alcohols such as ethylene glycol, 1,3-propylene glycol, 2,2-dimethylpropylene glycol and pentane-2,4-diol are particularly stable.

The reaction may be carried out without a solvent but may also be carried out in the presence of solvents.

Suitable solvents include aliphatic and aromatic hydrocarbons which are inert under the reaction conditions such as pentane, hexane, benzene and toluene and also ethers as for example tetrahydrofuran or ethylene glycol monomethyl ether and particularly strongly polar solvents such as acetonitrile, dimethylformamide and preferably dimethylsulfoxide.

The solvent may be used in an amount which is from twice to five times the weight of the starting components.

The process may be carried out batchwise in a stirred vessel or rocking autoclave or continuously in a reactor or cascade of reactors.

Atmospheric pressure or superatmospheric pressure up to 250 atmospheres may be used. It is of particular advantage to carry out the reaction under the vapor pressure of the reactants which is set up in a pressure-tight vessel under the reaction conditions.

In every case the reaction conditions are chosen so that the reaction proceeds in the liquid phase.

The reaction period for the reaction according to the invention is from five minutes to twenty hours, preferably from thirty minutes to ten hours, depending on the reaction temperature and the catalyst used.

The reaction mixture is generally worked up by fractional distillation.

By means of the process of the invention a number of high molecular weight $\alpha,\beta$-unsaturated aldehydes which have hitherto only been obtainable by expensive methods are obtained in a simple manner and in good yields; they are valuable intermediates for the production of various natural substances and odorants such as $\beta$-ionone, farnesol and phytol.

Thus for example citral obtainable according to the invention from dimethylacrolein and 3-methyl-2-buten-1-ol is a valuable intermediate for the production of $\beta$-ionone which is a key compound in the synthesis of vitamins A and E.

2,6,10-trimethyl-11-formyl-2,6,10-undecatrien-1-al-(2′,2′-dimethylpropylene)-acetal obtainable from dimethylacrolein and 2,6-dimethyl-8-hydroxy-2,6-octadien-1-al-(2′,2′-dimethylpropylene)-acetal is a valuable intermediate for the production of sinensal, the natural flavor and aroma of oranges.

The following Examples illustrate the invention. The parts specified in the Examples, unless otherwise stated, are by weight. Parts by volume bear the same relation to parts by weight as the liter to the kilogram.

EXAMPLE 1

100 parts of 3-methyl-2-buten-1-ol and 50 parts of 3,3-dimethylacrolein are heated for ninety minutes at 200°C and a pressure of 40 atmospheres in a rocking autoclave having a capacity of 250 parts by volume. The reaction product is worked up by distillation. 12.5 parts of citral is obtained having a boiling point of 104°C at 12 mm. The yield (based on 3,3-dimethylacrolein) is 53% of theory at a conversion of 26%.

EXAMPLE 2

A mixture of 600 parts of 3-methyl-2-buten-1-ol and 300 parts of 3,3-dimethylacrolein is pumped through a reactor having a capacity of 150 parts by volume with a residence time of seven minutes. The reaction temperature is 250°C and the pressure is 150 atmospheres. The reaction mixture which has reacted is fractionally distilled and 91.5 parts of citral is obtained. This is equivalent to a yield of 51% of theory based on 3,3dimethylacrolein at a conversion of 33%.

EXAMPLE 3

A mixture of 100 parts of geraniol and 100 parts of 3,3-dimethylacrolein is heated for ten hours in an autoclave having a capacity of 250 parts by volume at 180°C and at the autogenous pressure. The reaction product is worked up by distillation and 50.5 parts of farnesal is obtained having a boiling point of 122°C at 0.2 mm. The yield is 69% of theory based on 3,3-dimethylacrolein at a conversion of 28%.

EXAMPLE 4

A mixture of 160 parts of 3-methyl-2-buten-1-ol and 50 parts of citral is heated at 180°C in an autoclave having a capacity of 250 parts by volume for eight hours under the autogenous pressure. The reaction product is worked up by distillation. 40.5 parts of 3,7-dimethyl-4-(3'-methyl-2'-butenyl)-octa-2,6-dien-1-al is obtained having a boiling point of 98° to 99°C at 0.1 mm. The yield is 67% of theory at a conversion of 27% based on citral.

EXAMPLE 5

Air is blown for five minutes through a mixture of 100 parts of 3-methyl-2-buten-1-ol (prenol) and 100 parts of 3,3-dimethylacrolein. The reaction mixture containing peroxide is then heated for six hours at 140°C. The water formed in the reaction is removed continuously by injecting pentane into the reaction chamber. The rection product is worked up by distillation. 59.2 parts of citral having a boiling point of 103° to 106°C at 12 mm is obtained, equivalent to a yield of 76% of theory based on 3,3-dimethylacrolein at a conversion of 43%.

EXAMPLE 6

100 parts of 3-methyl-2-buten-1-ol is brought to refluxing temperature (140°C) and 100 parts of 3,3-dimethylacrolein in which 2 parts of dibenzoyl peroxide has been dissolved is introduced in the course of one hour while stirring. The reaction mixture is then heated for another three hours at 140°C, while the water formed is continuously removed using pentane as entrainer. Working up gives 105 parts of citral. The yield is thus 86% of theory based on 3,3-dimethylacrolein at a conversion of 67%.

EXAMPLE 7

A mixture of 100 parts of 3-methyl-2-buten-1-ol, 100 parts of 3,3-dimethylacrolein, 200 parts of ethylene glycol monomethyl ether and 3 parts of 30% aqueous hydrogen peroxide solution is heated under reflux for six hours while stirring and the water formed is removed continuously using pentane as entrainer. Fractional distillation of the reaction product gives 84.5 parts of citral, equivalent to a yield of 88% of theory, at a conversion of 53% (based on 3,3-dimethylacrolein).

EXAMPLE 8

100 parts of geraniol, 30 parts of 3,3-dimethylacrolein and 2.5 parts of propionic acid are heated together at refluxing temperature for four hours while stirring. The product is distilled. 83.5 parts of farnesal is obtained having a boiling point of 120° to 123°C at 0.2 mm. The yield is 84% of theory at a conversion of 63% (based on 3,3-dimethylacrolein).

EXAMPLE 9

A mixture of 140 parts of citral, 80 parts of 3-methyl-2-buten-1-ol and 3.3 parts of benzic acid is heated at 140°C for five hours. The water formed in the reaction is removed using hexane as entrainer. On working up, 122 parts of 3,7-dimethyl-4-(3'-methyl-2'-butenyl)-octa-2,6-dien-1-al is obtained having a boiling point of 98° to 101°C at 0.1 mm, equivalent to a yield of 86% of theory at a conversion of 70% (based on citral).

EXAMPLE 10

110 parts of geraniol, 50 parts of crotonaldehyde and 3.2 parts of t-butyl acetate are heated for six hours at 30 atmospheres pressure and at 150°C in an agitated autoclave having a capacity of 250 parts by volume. Working up gives 85 parts of 7,11-dimethyldodeca2,6,10-trien1-al having a boiling point of 93° to 96°C at 0.2 mm. The yield is 78% of theory at a conversion of 74% (based on crotonaldehyde).

EXAMPLE 11

A mixture of 50 parts of ionylidenethanol and 100 parts of 3,3-dimethylacrolein is heated for five hours at 130°C with 1.5 parts of acrylic acid, the water being formed being continuously removed with pentane. Excess 3,3-dimethylacrolein is first distilled off from the reaction product obtained. 29.9 parts of 3,7-dimethyl-1-(2',6',6'-trimethylcyclohex-2'-en-1-yl)-nona-1,3,7-trien9-al (dihydroretinal) is obtained in the form of yellow crystals from the residue by recrystallization from hexane. The yield is 82% of theory at a conversion of 56% (based on ionylidenethanol). The boiling point is 130° to 132°C at 10$^{-4}$ mm.

EXAMPLE 12

130 parts of 4-methyl-3-penten-2-ol and 110 parts of 3,3-dimethylacrolein are heated for three hours at 135°C with 3 parts of acrylic acid with azeotropic removal of the water formed. The reaction product is distilled. 115 parts of 4-methylcitral (2,4,6-trimethylocta-2,6-dien-8-al) is obtained having a boiling point of 96°to 98°C at 2 mm. Conversion is 63% and the yield is 84% (based on 3,3-dimethylacrolein).

EXAMPLE 13

50 parts of prenol and 50 parts of 3,3-dimethylacrolein have 3 parts of silica gel added and are heated for six hours at 135°C with azeotropic removal of water. The silica gel is then filtered off and the filtrate is distilled. 42.5 parts of citral is obtained, equivalent to a conversion of 66% and a yield of 71% (based on 3,3-dimethylacrolein).

EXAMPLE 14

A mixture of 187 parts of cinnamic alcohol, 360 parts of 3,3-dimethylacrolein and 550 parts of toluene is heated with 33 parts of glacial acetic acid in a V4A steel stirred vesel having a capacity of 5 liters for six hours at 140°C at a pressure of 2 atmospheres, the water forming being continuously removed as an azeotropic mixture with toluene. The product is distilled. 149 parts of 3-methyl-7-phenyl-2,6-heptadien-1-al is obtained having a boiling point of 118° to 120°C at 10⁻³ mm. The yield is 81% of theory (based on cinnamic alcohol) at a conversion of 66%.

EXAMPLE 15

400 parts of 3,3-dimethylacrolein and 130 parts of 2-methyl-4-hydroxy-2-buten-1-al-(2′,2′-dimethylpropylene)-acetal (the acetal of β-formylcrotyl alcohol with neopenthylglycol) are heated with 5 parts of acrylic acid at 137°C, the water which is forming being continuously removed by injecting pentane into the reaction chamber. The reaction mixture is worked up. 89.2 parts of 2,6-dimethyl-7-formyl-2,6-heptadien-1-al-(2′,2′-dimethylpropylene)-acetal is obtained having a boiling point of 120° to 122°C at 10⁻⁴ mm. The yield is 83% of theory at a conversion of 61% based on 2-methyl-4-hydroxy-2-buten-1-al-(2′,2′-dimethylpropylene)-acetal.

EXAMPLE 16

A mixture of 150 parts of 3,3-dimethylacrolein and 50 parts of 2,6-dimethyl-8-hydroxy-2,6-octadien-1-al-(2′,2′-dimethylpropylene)-acetal is heated with 2 parts of 3,3-dimethylacrylic acid for five hours at 132°C while entraining out the water formed with pentane. The subsequent working up of the reaction product gives 30.4 parts of 2,6,10-trimethyl-11-formyl-2,6,10-undecatrien-1-al-(2′,2′-dimethylpropylene)-acetal having a boiling point of 148° to 150°C at 10⁻⁴ mm. A yield of 78% of theory is obtained at a conversion of 60% (based on 2,6-dimethyl-8-hydroxy-2,6-octadien-1-al-(2′,2′-dimethylpropylene)-acetal).

EXAMPLE 17

60 parts of prenyl acetate, 40 parts of 3,3-dimethylacrolein and 2 parts of benzoic acid are heated together for five hours thirty minutes at 140°C and the product is worked up. 11.1 parts of citral is obtained having a boiling point of 104°C at 12 mm in a yield of 48% at a conversion of 32% (based on 3,3-dimethylacrolein).

EXAMPLE 18

A mixture of 100 parts of 3,3-dimethylacrolein, 200 parts of prenol and 150 parts of propionic acid is heated for three hours at 130°C, the water formed being distilled out azeotropically. The reaction product is worked up. 24 parts of citral is obtained. This is equivalent to a yield of 51% of theory at a conversion of 26% (based on 3,3-dimethylacrolein).

EXAMPLE 19

50 parts of 2-methyl-2-buten-1-al (tiglaldehyde), 50 parts of 3-methyl-2-buten-1-ol (prenol) and 100 parts of toluene are heated with 6 parts of propionic acid in a small stirred vessel for three hours at 3.6 atmospheres gauge pressure at 180°C while the water formed is removed azeotropically from the reaction chamber with toluene. In the subsequent working up 47 parts of 2,7-dimethyl-2,6-octadien-1-al is obtained having a boiling point of 36° to 38°C at 0.1 mm. The yield is 77% of theory at a conversion of 69% based on prenol.

EXAMPLE 20

50 parts of 2-methyl-4-hydroxy-2-buten-1-al-(2′,2′-dimethylpropylene)-acetal and 150 parts of 3,3-dimethylacrolein are mixed with 6 parts of 30% aqueous hydrogen peroxide solution and heated for five hours at temperatures of from 135° to 142°C, the water formed being distilled off continuously by supplying pentane. The reaction product is distilled. 36.4 parts of 2,6-dimethyl-7-formyl-2,6-heptadien-1-al-(2′,2′-dimethylpropylene)-acetal is obtained. This is equivalent to a yield of 79% of theory at a conversion of 68% based on 2-methyl-4-hydroxy-2-buten-1-al-(2′,2′-dimethylpropylene)-acetal.

EXAMPLE 21

A current of air is bubbled through a mixture of 200 parts of 3,3-dimethylacrolein and 100 parts of cinnamic alcohol for two minutes. The mixture is then heated at 135°C for four hours and the water thus formed is continuously removed from the reaction chamber by supplying cyclohexane. The reaction product is distilled. 65 parts of 3-methyl-7-phenyl-2,6-heptadien-1-al is obtained, equivalent to a yield of 75% at a conversion of 58% based on cinnamic alcohol.

We claim:
1. A process for the production of high molecular weight α,β-unsaturated aldehydes of the general formula (I):

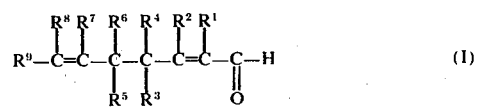

where
R¹ is hydrogen, alkyl of one to four carbon atoms, phenyl or phenyl bearing alkyl of one to four carbon atoms as a substituent;
R² is hydrogen, alkyl of one to four carbon atoms, phenyl or phenyl bearing alkyl of one to four carbon atoms as a substituent;
R³ is hydrogen or alkyl of one to four carbon atoms;
R⁵ is hydrogen or alkyl of one to four carbon atoms;
R⁶ is hydrogen or alkyl of one to four carbon atoms;
R⁷ is hydrogen or alkyl of one to four carbon atoms;
R⁴ is hydrogen or a saturated or unsaturated, branched or linear aliphatic or cycloaliphatic hydrocarbon radical of one to twelve carbon atoms;
R⁸ is alkyl of one to four carbon atoms or (when R⁹ is phenyl) hydrogen; and
R⁹ is a saturated or unsaturated branched or linear aliphatic or cycloaliphatic hydrocarbon radical of one to twelve carbon atoms, or phenyl
wherein an allyl compound of the formula (II):

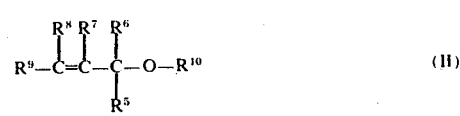

in which R⁵ to R⁹ have the meanings given above and R¹⁰ is hydrogen or acyl of a carboxylic acid of one to five carbon atoms is reacted in the liquid phase with an α,β-unsaturated aldehyde of the formula (III):

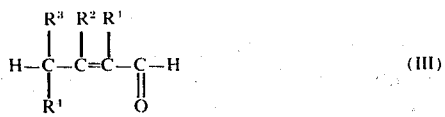

in which R¹ to R⁴ have the meanings given above, at elevated temperature of about 60°–300°C and in the presence of an acid catalyst wit a pK value of −9 to 6 in such an amount of such acid catalyst that the reaction mixture has a pH of 1 to 7.

2. A process as claimed in claim 1 carried out in the presence of 0.01 to 10% by weight based on the sum of the reactants of an acid of the pK from about 3 to 6 at a temperature of from 60° to 300°C.

3. A process as claimed in claim 2 wherein the amount of said acid is 0.1 to 3% by weight.

4. A process as claimed in claim 1 carried out in the presence of 0.01 to 1% by weight based on the sum of the reactants of an acid of a pK of from −9 to about 3 at a temperature of from 60° to 300°C.

5. A process as claimed in claim 4 wherein the amount of said acid used is from 0.01 to 0.5% by weight.

6. A process as claimed in claim 1 wherein water formed in the reaction is removed continuously from the reaction mixture.

7. A process as claimed in claim 1 carried out under the vapor pressure of the reactants which is set up in a pressuretight vessel under the reaction conditions.

8. A process as claimed in claim 1 wherein said allyl compound has the formula (IIa):

$$H-\left[CH_2-\underset{\underset{}{}}{C}=\underset{\underset{}{}}{C}-CH_2\right]_n-OH \qquad (IIa)$$

with CH₃ and R⁷ on the central carbons, in which $n$ is 1, 2 or 3 and R⁷ is hydrogen or methyl.

9. A process as claimed in claim 1 wherein an allyl compound of formula (II) is reacted with 3,3-dimethylacrolein.

10. A process as claimed in claim 1 wherein 3-methyl-2-buten-1-ol is reacted with 3,3-dimethylacrolein.

11. A process as claimed in claim 1 wherein geraniol is reacted with 3,3-dimethylacrolein.

12. A process as claimed in claim 1 wherein ionylidenethanol is reacted with 3,3-dimethylacrolein.

* * * * *

UNITED STATES PATENT AND TRADEMARK OFFICE
CERTIFICATE OF CORRECTION

PATENT NO. : 3,965,193

DATED : June 22, 1976

INVENTOR(S) : Norbert Goetz et al.

It is certified that error appears in the above-identified patent and that said Letters Patent are hereby corrected as shown below:

In Column 4, Line 37, delete " ..., salicyclic acid,..."
and substitute -- ..., salicylic acid,... --

In Column 8, Line 68, delete "... stirred vesel ..."
and substitute --... stirred vessel ... --

In Column 11, Line 9 (Claim 1), delete "... catalyst wit a..."
and substitute --... catalyst with a ... --

Signed and Sealed this

Fifteenth Day of March 1977

[SEAL]

Attest:

RUTH C. MASON
Attesting Officer

C. MARSHALL DANN
Commissioner of Patents and Trademarks